United States Patent [19]

de Castiglione et al.

[11] Patent Number: 4,474,765

[45] Date of Patent: Oct. 2, 1984

[54] BIOLOGICALLY ACTIVE PEPTIDES

[75] Inventors: Roberto de Castiglione, Milan; Giuseppe Perseo, Desio; Francesco Santangelo, Milan, all of Italy

[73] Assignee: Farmitalia Carlo Erba S.p.A., Milan, Italy

[21] Appl. No.: 481,298

[22] Filed: Apr. 1, 1983

[30] Foreign Application Priority Data

Apr. 13, 1982 [GB] United Kingdom ............... 8210696

[51] Int. Cl.$^3$ .................... A61K 37/00; C07C 103/52
[52] U.S. Cl. ............................ 424/177; 260/112.5 R
[58] Field of Search ................. 260/112.5 R; 424/177

[56] References Cited

U.S. PATENT DOCUMENTS 4,237,046 12/1980 Bodanszky .................. 260/112.5 R
4,261,886 4/1981 Goldstein et al. ........... 260/112.5 R
4,385,050 5/1983 Lederis et al. .............. 260/112.5 R

*Primary Examiner*—Delbert R. Phillips
*Attorney, Agent, or Firm*—Oblon, Fisher, Spivak, McClelland & Maier

[57] ABSTRACT

Peptides of the formula

X-A-Pro-Pro-Ile-Ser-B-C-Leu-D-E-F-G-W wherein

X is H, a terminal N atom protecting group of acyl, aromatic urethane, aliphatic urethane, alkyl or aralkyl type, or a residue of a natural L-amino acid, the free amino group of the residue optionally being protected by a terminal N atom protecting group as aforesaid;

A is a L-amino acid residue or a glycine residue;

B is a neutral L-amino acid residue;

C is a neutral L-amino acid residue or an acidic L-amino acid residue;

D is a L-amino acid residue which contains in the side chain an alcoholic hydroxyl group; the latter may be free or protected by a usual protecting group for the hydroxy function, said protecting group being t-butyl, trityl, benzyl, 2,4-dichloro-benzyl, benzyloxycarbonyl, 2-bromobenzyloxycarbonyl t-butoxycarbonyl or lower acyl;

E is a valence bond or a neutral L-amino acid residue;

F is a valence bond or a L-amino acid residue;

G is a valence bond or a neutral L-amino acid residue;

W is OH, $NH_2$, OR, NHR, $NR_2$ or NH—NH—R';

R is a straight chain, branched chain or cyclic (including fused or bridged ring), substituted or unsubstituted $C_1$-$C_{11}$ alkyl group, phenyl, or $C_6$-$C_8$ aralkyl;

R' is H, any value which R may have, a straight chain, branched chain or cyclic aliphatic $C_1$-$C_{11}$ acyl group (optionally substituted by OH, $NH_2$, or a halogen atom), a $C_3$-$C_8$ alkenyl group, an aromatic acyl group similarly optionally substituted, a straight chain, branched chain or cyclic aliphatic $C_3$-$C_{11}$ urethane type group or an aromatic urethane type group.

Phamaceutically acceptable salts of these peptides are also provided, as are pharmaceutical compositions containing peptides or their salts. The peptides can be prepared by classical solution synthesis or by solid phase synthesis on polymeric supports.

7 Claims, No Drawings

BIOLOGICALLY ACTIVE PEPTIDES

DESCRIPTION

The invention relates to biologically active peptides, their pharmaceutically acceptable salts, processes for their preparation and pharmaceutical compositions containing them.

The peptides of the invention are fragments or modified fragments of sauvagine, a natural peptide consisting of 40 amino acid residues (P. C. Montecucchi, A. Henschen—Int. J. Peptide Protein Res. 18, 113–120, 1981), which shows a series of interesting pharmacological activities, such as release of ACTH and β-endorphin, and inhibition of the release of growth hormone, TSH and prolactin (P. C. Montecucchi et al., "Hormone receptor in Digestion and Nutrition," G. Rosselin et al. eds., Elsevier/North-Holland Biomed. Press, 1979, 101–108).

It was surprisingly found that the peptides of the invention maintain totally or partially the biological activity spectrum of sauvagine. The importance of this discovery is evident. The synthesis of a tridecapeptide or a shorter homologue is, obviously, more easily realized than the synthesis of a peptide of 40 amino acid residues. Purer or more easily purifiable products are obtained.

In this specification symbols and abbreviations are those commonly used in peptide chemistry (see J. Biol. Chem., 1972, 247, 977–983).

The invention provides peptides of the general formula:

X-A-Pro-Pro-Ile-Ser-B-C-Leu-D-E-F-G-W wherein

X represents a hydrogen atom, a terminal nitrogen protecting group of acyl, aromatic urethane, alkyl, aralkyl or aliphatic urethane type or a residue of a neutral L-amino acid, the free amino group of the residue optionally being protected by a terminal nitrogen atom protecting group of the type cited above;

A represents a L-amino acid residue or a glycine residue;

B represents a neutral L-amino acid residue;

C represents a neutral L-amino acid residue or an acidic L-amino acid residue;

D represents a L-amino acid residue which contains in the side chain an alcoholic hydroxy group, which may be free or protected by a conventional hydroxy protecting group;

E represents a valence bond or a neutral L-amino acid residue;

F represents a valence bond or a L-amino acid residue;

G represents a valence bond or a neutral L-amino acid residue;

W represents a hydroxy group, an amino group or a group of the formula OR, NHR, NR$_2$ or NH—NH—R' wherein R represents a straight chain, branched chain or cyclic (including fused or bridged ring) alkyl group having up to 11 carbon atoms, and being substituted or unsubstituted, a phenyl group or an aralkyl group having from 7 to 9 carbon atoms; and R' represents a hydrogen atom, any of the groups which R may represent, an alkenyl group having 3 to 8 carbon atoms; a straight chain, branched chain or cyclic aliphatic acyl group having from 1 to 11 carbon atoms, unsubstituted or substituted by a hydroxy or amino group or a halogen atom, an aromatic acyl group, unsubstituted or substituted by a hydroxy or amino group or a halogen atom, a straight chain, branched chain or cyclic aliphatic urethane type group having from 3 to 11 carbon atoms, or an aromatic urethane type group.

Preferred terminal nitrogen atom protecting groups which X may represent include (of acyl type) formyl, acetyl, trifluoroacetyl, propionyl and benzoyl groups; (or aromatic urethane type) benzyloxycarbonyl (Z), 4-nitrobenzyloxycarbonyl, 4-methoxybenzyloxycarbonyl, 2,4-dichlorobenzyloxycarbonyl, 2-bromobenzyloxycarbonyl, 9-fluorenylmethoxycarbonyl (Fmoc) and 3,5-dimethoxy-α,α'-dimethylbenzyloxycarbonyl (Ddz) groups; (of aliphatic urethane type) t-butoxycarbonyl (Boc), 1-methyl-cyclobutoxycarbonyl, adamantyloxycarbonyl and isobornyloxycarbonyl groups; and (of alkyl and aralkyl type) trityl, benzyl (Bzl), methyl and isopropyl groups. Preferred neutral L-amino acid residues which X may represent include Pyr, Gln, Pro and 2-oxo-L-pipecolic acid.

Preferred L-amino acid residues which A may represent include Glu and Gln. Preferred neutral L-amino acid residues which B may represent include Ile, Leu, Nle, Val and Phe. Preferred neutral L-amino acid residues which C may represent include Asn and Gln; preferred acidic L-amino acid residues which C may represent include Asp and Glu. Preferred L-amino acid residues which D may represent include Ser, Hse, and Thr; if the hydroxy groups of a residue represented by D is protected, it is preferably protected by a t-butyl, trityl, benzyl, 2,4-dichlorobenzyl, benzyloxycarbonyl, 2-bromobenzyloxycarbonyl, tetrahydropyranyl or t-butoxycarbonyl group or by a lower acyl group such as a formyl, acetyl, trifluoroacetyl, propionyl or benzoyl group.

Preferred neutral L-amino acid residues which E may represent include Phe, Leu and Nle. Preferred L-amino acid residues which F may represent include Glu, Gln and His. Preferred neutral L-amino acid residues which G may represent include Leu and Phe.

Preferred groups which R may represent include methyl, ethyl, n-propyl, isopropyl, n-butyl, s-butyl, isobutyl, t-butyl, 2,2,2-trifluoroethyl, cyclohexyl, adamantyl, phenyl, benzyl and phenethyl groups. Examples of alkenyl groups which R' may represent include allyl and pentenyl groups. Examples of acyl groups which R' may represent are formyl, acetyl, trifluoroacetyl, propionyl, butyryl, adamantylcarbonyl, benzoyl, phenylacetyl and cinnamyl groups. The aliphatic and aromatic urethane type groups which R' may represent are preferably those groups mentioned as preferred terminal nitrogen protecting groups X of aliphatic and aromatic urethane type.

Salts of peptides according to the invention with pharmaceutically acceptable acids or bases are within the scope of the invention. Such acid addition salts can be derived from a variety of inorganic and organic acids as sulphuric, phosphoric, hydrochloric, hydrobromic, hydroiodic, nitric, sulphamic, citric, lactic, pyruvic, oxalic, maleic, succinic, tartaric, cinnamic, acetic, trifluoroacetic, benzoic, salicyclic, gluconic, ascorbic and related acids. Such base addition salts can be derived from a variety of inorganic and organic bases as sodium hydroxide, potassium hydroxide, diethylamine, triethylamine and dicyclohexylamine.

The synthesis of the peptides of the invention may be accomplished either by classical solution methods or by solid phase on polymeric supports. In the classical solution method the synthesis consists essentially in appropriate successive condensations of protected amino acids or peptides. The condensation is carried out so that the resulting peptides have the desired sequence of 9 to 13 amino acid residues. The amino acids and peptides, which are condensed according to methods known in themselves in polypeptide chemistry, have such of their amino and carboxy groups as are not involved in the formation of the peptide linkage blocked by a suitable protecting group. The hydroxy functions of hydroxy amino acids may be protected by suitable protecting groups (throughout all the synthesis or only during a few steps) or may be kept unprotected.

The protecting groups are capable of being removed by acidolysis, saponification or hydrogenolysis. For the protection of the amino groups the following protective groups may for example be employed: benzyloxycarbonyl, t-butoxycarbonyl, trityl, formyl, trifluoroacetyl, o-nitrophenylsulphenyl, 4-methoxybenzyloxycarbonyl, 9-fluorenylmethoxycarbonyl or 3,5-dimethoxy-$\alpha,\alpha'$-dimethylbenzyloxycarbonyl. For the protection of the carboxy groups the following protective groups may for example be employed: methyl, ethyl, t-butyl, benzyl or p-nitro-benzyl. For the protection of the hydroxy groups the following protecting groups may for example be used: acetyl, t-butoxycarbonyl, benzyloxycarbonyl, 2-bromobenzyloxycarbonyl, tetrahydropyranyl, t-butyl, trityl, benzyl or 2,4-dichlorobenzyl.

The condensation between an amino group of one molecule and a carboxyl group of another molecule to form the peptide linkage may be carried out through an activated acyl-derivative such as a mixed anhydride, an azide or an activated ester, or by direct condensation between a free amino group and a free carboxyl group, in the presence of a condensing agent such as dicyclohexylcarbodiimide, alone or together with a racemization preventing agent, such as N-hydroxysuccinimide or 1-hydroxybenzotriazole.

Hydrazido or substituted hydrazido derivatives according to the invention are prepared by condensation of the N-protected peptide or amino acid with a suitably substituted hydrazido such as benzylcarbazate, t-butylcarbazate, adamantylcarbazate, phenylhydrazine or adamantylhydrazine, or reacting the N-protected peptide or amino acid hydrazide with a suitable alkylating agent, such as an alkyl chloride, or with a suitable acylating agent such as benzylchloroformate, t-butylchloroformate, di-t-butyldicarbonate or adamantylfluoroformate.

The condensation may be carried out in a solvent such as dimethylformamide, pyridine, acetonitrile, tetrahydrofuran or N-methyl-2-pyrrolidone. The reaction temperature may be from $-30°$ C. to ambient temperature. The reaction time is generally from 1 to 120 hours. The scheme of synthesis, the protecting groups and the condensing agents are selected so as to avoid the risk of racemization.

Deprotecting reactions are carried out according to methods known per se in polypeptide chemistry. Peptides wherein W represents OR are prepared, for example, starting from the C-terminal amino acid esterified by the appropriate alcohol. Peptides wherein W represents OH can be prepared, for example, by hydrolysis of peptides wherein W represents OR. Peptides wherein W represents $NH_2$, NHR or $NR_2$ can be prepared by amynolysis of the corresponding esters or starting from a C-terminal amino acid amidated by an appropriate amine.

In the solid-phase method a polymeric support is used. The polymer is preferably a copolymer of styrene with from 1 to 2 percent by weight of divinyl benzene as a cross-linking agent which causes the polystyrene polymer to be completely insoluble in most organic solvents. The synthesis is commenced from the C-terminal end of the peptide, by attaching the required amino acid to a chloromethylated resin, a hydroxymethyl resin, or a benzhydrylamine resin. The amino and side chain protecting groups are those described in the classical solution synthesis.

In the preparation of the compounds of this invention, an amino protected amino acid is coupled to the chloromethylated resin via caesium salt, or to a hydroxymethyl or benzhydrylamine resin, with the aid of a condensing agent such as dicyclohexylcarbodiimide.

After the initial coupling, the amino protecting group is removed by a choice of reagents including trifluoroacetic acid or hydrogen chloride solutions in organic solvents at room temperature. After removal of the amino protecting group, the remaining protected amino acids are coupled stepwise in the desired order to obtain the desired peptide. Each protected amino acid is generally reacted in a 3-fold excess using an appropriate carboxy group activator such as dicyclohexylcarbodiimide in solution in, for example, methylene dichloride: dimethylformamide mixtures.

After the desired amino acid sequence has been completed, the peptide is removed from the resin support by treatment with a reagent such as hydrogen fluoride, which not only cleaves the peptides from the resin, but also cleaves most of the remaining side-chain protecting groups. When chloromethylated or hydroxymethylated resin is used, hydrogen fluoride treatment results in the formation of the free peptide acid (W=OH). When benzhydrylamine resin is used, hydrogen fluoride treatment results directly in the free peptide amide (W=$NH_2$). Alternatively, when the chloromethylated or hydroxymethylated resin is employed, the side-chain protected peptide can be cleaved by treatment of the peptide resin with ammonia or a mono- or di-alkylamine to give the desired side-chain protected amide, alkylamide or dialkylamide (W=$NH_2$, NHR, $NR_2$). Side-chain protection may then be removed by any of the methods known in the art. In preparing the esters of the present invention (W=OR), the resins used to prepare the acid (W=OH) are employed and the side-chain protected peptide is cleaved with a base and the appropriate alcohol. Side-chain protection is then removed in the usual way.

Alternatively, the peptide acids and amides can be obtained from the peptide esters by saponification or ammonolysis.

The compounds according to the invention show an interesting pharmacological activity on inhibition of prolactin release. The inhibition of prolactin secretion was determined both "in vitro" and "in vivo"; "in vitro" test by using pituitary cells (obtained from rat or beef) suspended in Bio-gel columns, "in vivo" test by measuring the inhibition on serum basal prolactin secretion in male rats and the inhibition of suckening stimulated prolactin secretion in lactating rats.

The inhibition of prolactin release was determined in vitro using the method described by P. J. Lowry in J. Endocrinol. 63, 163 (1974).

The peptides synthesized were able to inhibit by 60–80% prolactin secretion in isolated and perfused rat pitnitary cells at a condensation ranging from $10^{-4}$ to $10^{-6}$M.

The compounds according to the invention are endowed with anxiolytic activity determined by modifications of the qualitative and quantitative spontaneous activity in rats according to the method described by A. E. whimbey and V. H. Denenberg in J. Comparative Physiology and Psychology, 63, 500–504 (1967).

The synthesized compounds, administered subcutaneously to rat at doses ranging from 20 mcg to 100 mcg/kg were able to decrease the level of anxiety induced by a new environment (open-field), and to increase explorativity in familiar enviroments (residential cages).

The invention further provides a pharmaceutical composition comprising a compound of the present invention or a pharmaceutically acceptable salt thereof in admixture with a pharmaceutically acceptable diluent or carrier; in addition, these preparations can have direct or delayed liberation of the active ingredient.

The preferred peptides according to the invention are the following:

1. H-Pyr-Gly-Pro-Pro-Ile-Ser-Ile-Asp-Leu-Ser-Leu-Glu-Leu-OH
2. H-Pyr-Gly-Pro-Pro-Ile-Ser-Ile-Asp-Leu-Ser-Leu-Glu-Leu-NH$_2$
3. H-Pyr-Gly-Pro-Pro-Ile-Ser-Ile-Asp-Leu-Ser-Leu-Glu-Phe-OH
4. H-Pyr-Gly-Pro-Pro-Ile-Ser-Ile-Asp-Leu-Ser-Leu-Glu-Phe-NH$_2$
5. H-Pyr-Gly-Pro-Pro-Ile-Ser-Ile-Asp-Leu-Ser-Leu-Gln-Leu-OH
6. H-Pyr-Gly-Pro-Pro-Ile-Ser-Ile-Asp-Leu-Ser-Leu-Gln-Leu-NH$_2$
7. H-Pyr-Gly-Pro-Pro-Ile-Ser-Ile-Asp-Leu-Ser-Leu-His-Leu-OH
8. H-Pyr-Gly-Pro-Pro-Ile-Ser-Ile-Asp-Leu-Ser-Leu-His-Leu-NH$_2$
9. H-Pyr-Gly-Pro-Pro-Ile-Ser-Ile-Asp-Leu-Ser-Phe-Glu-Leu-OH
10. H-Pyr-Gly-Pro-Pro-Ile-Ser-Ile-Asp-Leu-Ser-Phe-Glu-Leu-NH$_2$
11. H-Pyr-Gly-Pro-Pro-Ile-Ser-Ile-Asp-Leu-Thr-Leu-Glu-Leu-OH
12. H-Pyr-Gly-Pro-Pro-Ile-Ser-Ile-Asp-Leu-Thr-Leu-Glu-Leu-NH$_2$
13. H-Pyr-Gly-Pro-Pro-Ile-Ser-Ile-Asn-Leu-Ser-Leu-Glu-Leu-OH
14. H-Pyr-Gly-Pro-Pro-Ile-Ser-Ile-Asn-Leu-Ser-Leu-Glu-Leu-NH$_2$
15. H-Pyr-Gly-Pro-Pro-Ile-Ser-Ile-Glu-Leu-Ser-Leu-Glu-Leu-OH
16. H-Pyr-Gly-Pro-Pro-Ile-Ser-Ile-Glu-Leu-Ser-Leu-Glu-Leu-NH$_2$
17. H-Pyr-Gly-Pro-Pro-Ile-Ser-Leu-Asp-Leu-Ser-Leu-Glu-Leu-OH
18. H-Pyr-Gly-Pro-Pro-Ile-Ser-Leu-Asp-Leu-Ser-Leu-Glu-Leu-NH$_2$
19. H-Pyr-Gly-Pro-Pro-Ile-Ser-Phe-Asp-Leu-Ser-Leu-Glu-Leu-OH
20. H-Pyr-Gly-Pro-Pro-Ile-Ser-Phe-Asp-Leu-Ser-Leu-Glu-Leu-NH$_2$
21. H-Pyr-Glu-Pro-Pro-Ile-Ser-Ile-Asp-Leu-Ser-Leu-Glu-Leu-OH
22. H-Pyr-Glu-Pro-Pro-Ile-Ser-Ile-Asp-Leu-Ser-Leu-Glu-Leu-NH$_2$
23. H-Pyr-Gln-Pro-Pro-Ile-Ser-Ile-Asp-Leu-Ser-Leu-Glu-Leu-OH
24. H-Pyr-Gln-Pro-Pro-Ile-Ser-Ile-Asp-Leu-Ser-Leu-Glu-Leu-NH$_2$
25. H-Gln-Gly-Pro-Pro-Ile-Ser-Ile-Asp-Leu-Ser-Leu-Glu-Leu-OH
26. H-Gln-Gly-Pro-Pro-Ile-Ser-Ile-Asp-Leu-Ser-Leu-Glu-Leu-NH$_2$
27. H-Pyr-Gly-Pro-Pro-Ile-Ser-Ile-Asp-Leu-Ser-Phe-His-Leu-OH
28. H-Pyr-Gly-Pro-Pro-Ile-Ser-Ile-Asp-Leu-Ser-Phe-His-Leu-NH$_2$
29. H-Pyr-Gly-Pro-Pro-Ile-Ser-Ile-Asp-Leu-Thr-Phe-His-Leu-OH
30. H-Pyr-Gly-Pro-Pro-Ile-Ser-Ile-Asp-Leu-Thr-Phe-His-Leu-NH$_2$
31. H-Pyr-Gly-Pro-Pro-Ile-Ser-Leu-Asp-Leu-Thr-Phe-His-Leu-OH
32. H-Pyr-Gly-Pro-Pro-Ile-Ser-Leu-Asp-Leu-Thr-Phe-His-Leu-NH$_2$
33. H-Pyr-Glu-Pro-Pro-Ile-Ser-Leu-Asp-Leu-Thr-Phe-His-Leu-OH
34. H-Pyr-Glu-Pro-Pro-Ile-Ser-Leu-Asp-Leu-Thr-Phe-His-Leu-NH$_2$
35. H-Gln-Glu-Pro-Pro-Ile-Ser-Leu-Asp-Leu-Thr-Phe-His-Leu-OH
36. H-Gln-Glu-Pro-Pro-Ile-Ser-Leu-Asp-Leu-Thr-Phe-His-Leu-NH$_2$
37. H-Gln-Glu-Pro-Pro-Ile-Ser-Ile-Asp-Leu-Ser-Leu-Glu-Leu-OH
38. H-Gln-Glu-Pro-Pro-Ile-Ser-Ile-Asp-Leu-Ser-Leu-Glu-Leu-NH$_2$
39. H-Gln-Glu-Pro-Pro-Ile-Ser-Leu-Asp-Leu-Ser-Leu-Glu-Leu-OH
40. H-Gln-Glu-Pro-Pro-Ile-Ser-Leu-Asp-Leu-Ser-Leu-Glu-Leu-NH$_2$
41. H-Gln-Glu-Pro-Pro-Ile-Ser-Leu-Asp-Leu-Thr-Leu-Glu-Leu-OH
42. H-Gln-Glu-Pro-Pro-Ile-Ser-Leu-Asp-Leu-Thr-Leu-Glu-Leu-NH$_2$
43. H-Gln-Glu-Pro-Pro-Ile-Ser-Leu-Asp-Leu-Thr-Phe-Glu-Leu-OH
44. H-Gln-Glu-Pro-Pro-Ile-Ser-Leu-Asp-Leu-Thr-Phe-Glu-Leu-NH$_2$
45. H-Pyr-Gly-Pro-Pro-Ile-Ser-Ile-Asp-Leu-Ser-Leu-Glu-OH
46. H-Pyr-Gly-Pro-Pro-Ile-Ser-Ile-Asp-Leu-Ser-Leu-Glu-NH$_2$
47. H-Pyr-Gly-Pro-Pro-Ile-Ser-Ile-Asp-Leu-Ser-Leu-His-OH
48. H-Pyr-Gly-Pro-Pro-Ile-Ser-Ile-Asp-Leu-Ser-Leu-His-NH$_2$
49. H-Pyr-Gly-Pro-Pro-Ile-Ser-Ile-Asp-Leu-Ser-Phe-Glu-OH
50. H-Pyr-Gly-Pro-Pro-Ile-Ser-Ile-Asp-Leu-Ser-Phe-Glu-NH$_2$
51. H-Pyr-Gly-Pro-Pro-Ile-Ser-Ile-Asp-Leu-Thr-Leu-Glu-OH

52. H-Pyr-Gly-Pro-Pro-Ile-Ser-Ile-Asp-Leu-Thr-Leu-Glu-NH₂
53. H-Pyr-Gly-Pro-Pro-Ile-Ser-Ile-Asn-Leu-Ser-Leu-Glu-OH
54. H-Pyr-Gly-Pro-Pro-Ile-Ser-Ile-Asn-Leu-Ser-Leu-Glu-NH₂
55. H-Pyr-Gly-Pro-Pro-Ile-Ser-Ile-Glu-Leu-Ser-Leu-Glu-OH
56. H-Pyr-Gly-Pro-Pro-Ile-Ser-Ile-Glu-Leu-Ser-Leu-Glu-NH₂
57. H-Pyr-Gly-Pro-Pro-Ile-Ser-Leu-Asp-Leu-Ser-Leu-Glu-OH
58. H-Pyr-Gly-Pro-Pro-Ile-Ser-Leu-Asp-Leu-Ser-Leu-Glu-NH₂
59. H-Pyr-Gly-Pro-Pro-Ile-Ser-Phe-Asp-Leu-Ser-Leu-Glu-OH
60. H-Pyr-Gly-Pro-Pro-Ile-Ser-Phe-Asp-Leu-Ser-Leu-Glu-NH₂
61. H-Pyr-Glu-Pro-Pro-Ile-Ser-Ile-Asp-Leu-Ser-Leu-Glu-OH
62. H-Pyr-Glu-Pro-Pro-Ile-Ser-Ile-Asp-Leu-Ser-Leu-Glu-NH₂
63. H-Pyr-Gln-Pro-Pro-Ile-Ser-Ile-Asp-Leu-Ser-Leu-Glu-OH
64. H-Pyr-Gln-Pro-Pro-Ile-Ser-Ile-Asp-Leu-Ser-Leu-Glu-NH₂
65. H-Gln-Gly-Pro-Pro-Ile-Ser-Ile-Asp-Leu-Ser-Leu-Glu-OH
66. H-Gln-Gly-Pro-Pro-Ile-Ser-Ile-Asp-Leu-Ser-Leu-Glu-NH₂
67. H-Gln-Glu-Pro-Pro-Ile-Ser-Leu-Asp-Leu-Thr-Phe-His-OH
68. H-Gln-Glu-Pro-Pro-Ile-Ser-Leu-Asp-Leu-Thr-Phe-His-NH₂
69. H-Pyr-Gly-Pro-Pro-Ile-Ser-Ile-Asp-Leu-Ser-Leu-OH
70. H-Pyr-Gly-Pro-Pro-Ile-Ser-Ile-Asp-Leu-Ser-Leu-NH₂
71. H-Pyr-Gly-Pro-Pro-Ile-Ser-Ile-Asp-Leu-Ser-Phe-OH
72. H-Pyr-Gly-Pro-Pro-Ile-Ser-Ile-Asp-Leu-Ser-Phe-NH₂
73. H-Pyr-Gly-Pro-Pro-Ile-Ser-Ile-Asp-Leu-Thr-Leu-OH
74. H-Pyr-Gly-Pro-Pro-Ile-Ser-Ile-Asp-Leu-Thr-Leu-NH₂
75. H-Pyr-Gly-Pro-Pro-Ile-Ser-Ile-Asn-Leu-Ser-Leu-OH
76. H-Pyr-Gly-Pro-Pro-Ile-Ser-Ile-Asn-Leu-Ser-Leu-NH₂
77. H-Pyr-Gly-Pro-Pro-Ile-Ser-Ile-Glu-Leu-Ser-Leu-OH
78. H-Pyr-Gly-Pro-Pro-Ile-Ser-Ile-Glu-Leu-Ser-Leu-NH₂
79. H-Pyr-Gly-Pro-Pro-Ile-Ser-Leu-Asp-Leu-Ser-Leu-OH
80. H-Pyr-Gly-Pro-Pro-Ile-Ser-Leu-Asp-Leu-Ser-Leu-NH₂
81. H-Pyr-Gly-Pro-Pro-Ile-Ser-Phe-Asp-Leu-Ser-Leu-OH
82. H-Pyr-Gly-Pro-Pro-Ile-Ser-Phe-Asp-Leu-Ser-Leu-NH₂
83. H-Pyr-Glu-Pro-Pro-Ile-Ser-Ile-Asp-Leu-Ser-Leu-OH
84. H-Pyr-Glu-Pro-Pro-Ile-Ser-Ile-Asp-Leu-Ser-Leu-NH₂
85. H-Pyr-Gln-Pro-Pro-Ile-Ser-Ile-Asp-Leu-Ser-Leu-OH
86. H-Pyr-Gln-Pro-Pro-Ile-Ser-Ile-Asp-Leu-Ser-Leu-NH₂
87. H-Gln-Gly-Pro-Pro-Ile-Ser-Ile-Asp-Leu-Ser-Leu-OH
88. H-Gln-Gly-Pro-Pro-Ile-Ser-Ile-Asp-Leu-Ser-Leu-NH₂
89. H-Gln-Glu-Pro-Pro-Ile-Ser-Leu-Asp-Leu-Thr-Phe-OH
90. H-Gln-Glu-Pro-Pro-Ile-Ser-Leu-Asp-Leu-Thr-Phe-NH₂
91. H-Pyr-Gly-Pro-Pro-Ile-Ser-Ile-Asp-Leu-Ser-OH
92. H-Pyr-Gly-Pro-Pro-Ile-Ser-Ile-Asp-Leu-Ser-NH₂
93. H-Pyr-Gly-Pro-Pro-Ile-Ser-Ile-Asp-Leu-Thr-OH
94. H-Pyr-Gly-Pro-Pro-Ile-Ser-Ile-Asp-Leu-Thr-NH₂
95. H-Pyr-Gly-Pro-Pro-Ile-Ser-Ile-Asn-Leu-Ser-OH
96. H-Pyr-Gly-Pro-Pro-Ile-Ser-Ile-Asn-Leu-Ser-NH₂
97. H-Pyr-Gly-Pro-Pro-Ile-Ser-Ile-Glu-Leu-Ser-OH
98. H-Pyr-Gly-Pro-Pro-Ile-Ser-Ile-Glu-Leu-Ser-NH₂
99. H-Pyr-Gly-Pro-Pro-Ile-Ser-Leu-Asp-Leu-Ser-OH
100. H-Pyr-Gly-Pro-Pro-Ile-Ser-Leu-Asp-Leu-Ser-NH₂
101. H-Pyr-Gly-Pro-Pro-Ile-Ser-Phe-Asp-Leu-Ser-OH
102. H-Pyr-Gly-Pro-Pro-Ile-Ser-Phe-Asp-Leu-Ser-NH₂
103. H-Pyr-Glu-Pro-Pro-Ile-Ser-Ile-Asp-Leu-Ser-OH
104. H-Pyr-Glu-Pro-Pro-Ile-Ser-Ile-Asp-Leu-Ser-NH₂
105. H-Pyr-Gln-Pro-Pro-Ile-Ser-Ile-Asp-Leu-Ser-OH
106. H-Pyr-Gln-Pro-Pro-Ile-Ser-Ile-Asp-Leu-Ser-NH₂
107. H-Gln-Gly-Pro-Pro-Ile-Ser-Ile-Asp-Leu-Ser-OH
108. H-Gln-Gly-Pro-Pro-Ile-Ser-Ile-Asp-Leu-Ser-NH₂
109. H-Gln-Glu-Pro-Pro-Ile-Ser-Leu-Asp-Leu-Thr-OH
110. H-Gln-Glu-Pro-Pro-Ile-Ser-Leu-Asp-Leu-Thr-NH₂
111. H-Gly-Pro-Pro-Ile-Ser-Ile-Asp-Leu-Ser-OH
112. H-Gly-Pro-Pro-Ile-Ser-Ile-Asp-Leu-Ser-NH₂
113. H-Gly-Pro-Pro-Ile-Ser-Ile-Asp-Leu-Thr-OH
114. H-Gly-Pro-Pro-Ile-Ser-Ile-Asp-Leu-Thr-NH₂
115. H-Gly-Pro-Pro-Ile-Ser-Ile-Asn-Leu-Ser-OH
116. H-Gly-Pro-Pro-Ile-Ser-Ile-Asn-Leu-Ser-NH₂
117. H-Gly-Pro-Pro-Ile-Ser-Ile-Glu-Leu-Ser-OH
118. H-Gly-Pro-Pro-Ile-Ser-Ile-Glu-Leu-Ser-NH₂
119. H-Gly-Pro-Pro-Ile-Ser-Leu-Asp-Leu-Ser-OH
120. H-Gly-Pro-Pro-Ile-Ser-Leu-Asp-Leu-Ser-NH₂
121. H-Gly-Pro-Pro-Ile-Ser-Phe-Asp-Leu-Ser-OH
122. H-Gly-Pro-Pro-Ile-Ser-Phe-Asp-Leu-Ser-NH₂
123. H-Glu-Pro-Pro-Ile-Ser-Ile-Asp-Leu-Ser-OH
124. H-Glu-Pro-Pro-Ile-Ser-Ile-Asp-Leu-Ser-NH₂
125. H-Glu-Pro-Pro-Ile-Ser-Leu-Asp-Leu-Thr-OH

126. H-Glu-Pro-Pro-Ile-Ser-Leu-Asp-Leu-Thr-NH₂
127. H-Gly-Pro-Pro-Ile-Ser-Ile-Asp-Leu-Ser-Leu-OH
128. H-Gly-Pro-Pro-Ile-Ser-Ile-Asp-Leu-Ser-Leu-NH₂
129. H-Gly-Pro-Pro-Ile-Ser-Ile-Asp-Leu-Ser-Phe-OH
130. H-Gly-Pro-Pro-Ile-Ser-Ile-Asp-Leu-Ser-Phe-NH₂
131. H-Gly-Pro-Pro-Ile-Ser-Ile-Asp-Leu-Thr-Leu-OH
132. H-Gly-Pro-Pro-Ile-Ser-Ile-Asp-Leu-Thr-Leu-NH₂
133. H-Gly-Pro-Pro-Ile-Ser-Ile-Asn-Leu-Ser-Leu-OH
134. H-Gly-Pro-Pro-Ile-Ser-Ile-Asn-Leu-Ser-Leu-NH₂
135. H-Gly-Pro-Pro-Ile-Ser-Ile-Glu-Leu-Ser-Leu-OH
136. H-Gly-Pro-Pro-Ile-Ser-Ile-Glu-Leu-Ser-Leu-NH₂
137. H-Gly-Pro-Pro-Ile-Ser-Leu-Asp-Leu-Ser-Leu-OH
138. H-Gly-Pro-Pro-Ile-Ser-Leu-Asp-Leu-Ser-Leu-NH₂
139. H-Gly-Pro-Pro-Ile-Ser-Phe-Asp-Leu-Ser-Leu-OH
140. H-Gly-Pro-Pro-Ile-Ser-Phe-Asp-Leu-Ser-Leu-NH₂
141. H-Glu-Pro-Pro-Ile-Ser-Ile-Asp-Leu-Ser-Leu-OH
142. H-Glu-Pro-Pro-Ile-Ser-Ile-Asp-Leu-Ser-Leu-NH₂
143. H-Glu-Pro-Pro-Ile-Ser-Leu-Asp-Leu-Thr-Phe-OH
144. H-Glu-Pro-Pro-Ile-Ser-Leu-Asp-Leu-Thr-Phe-NH₂
145. H-Gly-Pro-Pro-Ile-Ser-Ile-Asp-Leu-Ser-Leu-Glu-OH
146. H-Gly-Pro-Pro-Ile-Ser-Ile-Asp-Leu-Ser-Leu-Glu-NH₂
147. H-Gly-Pro-Pro-Ile-Ser-Ile-Asp-Leu-Ser-Leu-His-OH
148. H-Gly-Pro-Pro-Ile-Ser-Ile-Asp-Leu-Ser-Leu-His-NH₂
149. H-Gly-Pro-Pro-Ile-Ser-Ile-Asp-Leu-Ser-Phe-Glu-OH
150. H-Gly-Pro-Pro-Ile-Ser-Ile-Asp-Leu-Ser-Phe-Glu-NH₂
151. H-Gly-Pro-Pro-Ile-Ser-Ile-Asp-Leu-Thr-Leu-Glu-OH
152. H-Gly-Pro-Pro-Ile-Ser-Ile-Asp-Leu-Thr-Leu-Glu-NH₂
153. H-Gly-Pro-Pro-Ile-Ser-Ile-Asn-Leu-Ser-Leu-Glu-OH
154. H-Gly-Pro-Pro-Ile-Ser-Ile-Asn-Leu-Ser-Leu-Glu-NH₂
155. H-Gly-Pro-Pro-Ile-Ser-Ile-Glu-Leu-Ser-Leu-Glu-OH
156. H-Gly-Pro-Pro-Ile-Ser-Ile-Glu-Leu-Ser-Leu-Glu-NH₂
157. H-Gly-Pro-Pro-Ile-Ser-Leu-Asp-Leu-Ser-Leu-Glu-OH
158. H-Gly-Pro-Pro-Ile-Ser-Leu-Asp-Leu-Ser-Leu-Glu-NH₂
159. H-Gly-Pro-Pro-Ile-Ser-Phe-Asp-Leu-Ser-Leu-Glu-OH
160. H-Gly-Pro-Pro-Ile-Ser-Phe-Asp-Leu-Ser-Leu-Glu-NH₂
161. H-Glu-Pro-Pro-Ile-Ser-Ile-Asp-Leu-Ser-Leu-Glu-OH
162. H-Glu-Pro-Pro-Ile-Ser-Ile-Asp-Leu-Ser-Leu-Glu-NH₂
163. H-Glu-Pro-Pro-Ile-Ser-Leu-Asp-Leu-Thr-Phe-His-OH
164. H-Glu-Pro-Pro-Ile-Ser-Leu-Asp-Leu-Thr-Phe-His-NH₂
165. H-Gly-Pro-Pro-Ile-Ser-Ile-Asp-Leu-Ser-Leu-Glu-Leu-OH
166. H-Gly-Pro-Pro-Ile-Ser-Ile-Asp-Leu-Ser-Leu-Glu-Leu-NH₂
167. H-Gly-Pro-Pro-Ile-Ser-Ile-Asp-Leu-Ser-Leu-Glu-Phe-OH
168. H-Gly-Pro-Pro-Ile-Ser-Ile-Asp-Leu-Ser-Leu-Glu-Phe-NH₂
169. H-Gly-Pro-Pro-Ile-Ser-Ile-Asp-Leu-Ser-Leu-His-Leu-OH
170. H-Gly-Pro-Pro-Ile-Ser-Ile-Asp-Leu-Ser-Leu-His-Leu-NH₂
171. H-Gly-Pro-Pro-Ile-Ser-Ile-Asp-Leu-Ser-Phe-Glu-Leu-OH
172. H-Gly-Pro-Pro-Ile-Ser-Ile-Asp-Leu-Ser-Phe-Glu-Leu-NH₂
173. H-Gly-Pro-Pro-Ile-Ser-Ile-Asp-Leu-Thr-Leu-Glu-Leu-OH
174. H-Gly-Pro-Pro-Ile-Ser-Ile-Asp-Leu-Thr-Leu-Glu-Leu-NH₂
175. H-Gly-Pro-Pro-Ile-Ser-Ile-Asn-Leu-Ser-Leu-Glu-Leu-OH
176. H-Gly-Pro-Pro-Ile-Ser-Ile-Asn-Leu-Ser-Leu-Glu-Leu-NH₂
177. H-Gly-Pro-Pro-Ile-Ser-Ile-Glu-Leu-Ser-Leu-Glu-Leu-OH
178. H-Gly-Pro-Pro-Ile-Ser-Ile-Glu-Leu-Ser-Leu-Glu-Leu-NH₂
179. H-Gly-Pro-Pro-Ile-Ser-Leu-Asp-Leu-Ser-Leu-Glu-Leu-OH
180. H-Gly-Pro-Pro-Ile-Ser-Leu-Asp-Leu-Ser-Leu-Glu-Leu-NH₂
181. H-Gly-Pro-Pro-Ile-Ser-Phe-Asp-Leu-Ser-Leu-Glu-Leu-OH
182. H-Gly-Pro-Pro-Ile-Ser-Phe-Asp-Leu-Ser-Leu-Glu-Leu-NH₂
183. H-Glu-Pro-Pro-Ile-Ser-Ile-Asp-Leu-Ser-Leu-Glu-Leu-OH
184. H-Glu-Pro-Pro-Ile-Ser-Ile-Asp-Leu-Ser-Leu-Glu-Leu-NH₂
185. H-Glu-Pro-Pro-Ile-Ser-Leu-Asp-Leu-Thr-Phe-His-Leu-OH
186. H-Glu-Pro-Pro-Ile-Ser-Leu-Asp-Leu-Thr-Phe-His-Leu-NH₂

The following Examples illustrate the invention. The Rf values were determined on pre-coated plates of silica gel 60 $F_{254}$ (Merck) Layer thickness 0.25 mm, length 20 cm, using the following development systems:
System A:
n-butanol:acetic acid:water
(4:1:1 by volume)
System B:
chloroform:methanol:32% ammonium hydroxide
(65:45:20 by volume)

"Merck" is a Trade Mark.

TLC analysis were carried out at a temperature ranging from 18° to 25° C., the R1 values can therefore change ±5%.

High pressure liquid chromatography (HPLC) analysis were carried out on column Hibar Lichrosorb R9-18 (5μ) using Eluent A: KH$_2$PO$_4$ 0.02M, pH 7, 10% acetonitrile
Eluent B: KH$_2$PO$_4$ 0.02M, pH 7, 60% acetonitrile
Mobile phase: mix A and B to obtain a solution containing 10% B. Increase percent of B from 10% to 60% in 25 minutes.

High voltage paper electrophoresis is carried out with a Pherograph-Original-Frankfurt Type 64 apparatus on Schleicher and Schull paper No. 2317 at pH 5,8 (pyridine:acetic acid:water 45:5:450 by volume)32,5 V/cm). Electrophoretic mobilities (E$_{5.8}$) are given relative to glutamic acid.

Synthesis on a polymeric support can be carried out, for example, by one of the following procedures.

Procedure A. Preparation of Boc—(AA)$_n$—(AA)$_{n-1}$ . . . (AA)$_1$-Hydroxymethyl Polystyrene Ester Chloromethylated polystyrene resin is esterified with the first Boc-amino acid (Boc—AA$_1$—OH) according to Gisin, Helv. Chim. Acta, 56, 1476 (1973). The polystyrene ester is treated according to schedule A for incorporation of Boc—(AA)$_2$—OH . . . Boc(AA)$_n$—OH to give the title resin.

Schedule A

1. Wash 3 times with dichloromethane.
2. Treat twice for 1 minute with trifluoroacetic acid:-dichloromethane (40:60 by volume).
3. Treat for 30 minutes with trifluoroacetic acid:dichloromethane (40:60 by volume).
4. Wash 4 times with dichloroethane.
5. Treat twice for 1 minute with 10% N-methylmorpholine in dichloromethane.
6. Treat for 5 minutes with 10% N-methylmorpholine in dichloromethane.
7. Wash 8 times with dichloromethane.
8. Add 2 or 3 equivalents of the symmetric anhydride of the corresponding amino acid derivative, prepared according to Hagenmayer and Frank, Hoppe-Seyler's Z Physiol. Chem., 353, 1973, (1972), dissolved in dichloromethane. Reaction time 0.5 to 2 hours.
9. Wash 3 times with dichloromethane.
10. Wash 3 times with isopropanol.
11. Wash 3 times with dichloromethane.
12. Test by the ninhydrin reaction according to Kaiser et al., Annal. Biochem., 34, 595, (1970). In case of incomplete reaction repeat steps 4 to 11.

Procedure B. Preparation of H—(AA)$_n$—(AA)$_{n-1}$ . . . (AA)$_1$-Hydroxymethyl Polystyrene Ester After introduction of the last amino acid derivative according to schedule A (procedure A), repeat steps 1 to 7 of schedule A, and wash 4 times with isopropanol.

Procedure C. Preparation of Boc—(AA)$_n$—(AA)$_{n-1}$ . . . (AA)$_1$-Benzhydrylamine Resin Boc—(AA)$_1$—OH is attached to a benzhydrylamine resin via dicyclohexylcarbodiimide, as described by Pietta et al., J. Org. Chem. 39, 44 (1974). Unreacted amino groups are acetylated with acetic anhydride:-pyridine:dichloromethane (2:1:10 by volume). The polystyrene amide is then treated according to schedule A (procedure A) for the incorporation of the other amino acid residues to give the title resin.

Procedure D. Preparation of H—(AA)$_{n-1}$ . . . (AA)$_1$-Benzhydrylamine Resin. Operate as in procedure B starting from the peptide resin of procedure C

EXAMPLE 1

Pyr-Gly-Pro-Pro-Ile-Ser-Ile-Asp-Leu-Ser-Leu-Glu-Leu-OH sodium salt (1)

1 g of peptide resin detained by procedure A with the required sequence of amino acid residues (introduced as Boc-Leu-OH, Boc-Glu(OBzl)-OH, Boc-Leu-OH, Boc-Ser(Bzl)-OH, Boc-Leu-OH, Boc-Asp(OBzl)-OH, Boc-Ile-OH, Boc-Ser(Bzl)-OH, Boc-Ile-OH, Boc-Pro-OH, Boc-Pro-OH, Boc-Gly-OH, H-Pyr-OH in that order) was suspended for 1 hour at 0° C. in 10 ml of anhydrous (distilled over 500 mg of cobalt trifluoride) hydrogen fluoride containing 1 ml of anisole.

The idrogen fluoride was removed under reduced pressure and the anisole was removed by washing with diisopropyl ether (3×10 ml). The crude peptide was extracted from the resin with dimethylformamide (3×10 ml) and purified by gel filtration on Sephadex LH-20 using dimethylformamide as eluent, and by an exchange chromatography on DEAE-Sephadex A-25 using as eluent ammonium acetate buffer at pH 6. The product was then transformed to the sodium salt with an excess of sodium bicarbonate, desalted on Sephadex G-15, and lyophilized.

0.120 g of peptide (1) were obtained.

R1$_A$ 0.17; Rf$_B$ 0.44; E$_{58}$ 0.60 Glu; R$_t$ (HPLC) ca.15'

Amino acid ratio: Asp 0.99; Ser. 1.94; Glu 1.96; Pro 1.98; Gly 1.01; Leu 2.96; Ile 1.97.

EXAMPLE 2

Pyr-Gly-Pro-Pro-Ile-Ser-Ile-Asp-Leu-Ser-Leu-Glu-Leu-NH$_2$ Sodium salt (2)

1 g of peptide resin obtained by procedure C with the required sequence of amino acid residues (introduced as Boc-Leu-OH, Boc-Glu(OBzl)-OH, Boc-Leu-OH, Boc-Ser-(Bzl)-OH, Boc-Leu-OH, Boc-Asp(OBzl)-OH, Boc-Ile-OH, Boc-Ser(Bzl)-OH, Boc-Ile-OH, Boc-Pro-OH, Boc-Pro-OH, Boc-Gly-OH, H-Pyr-OH, in that order) was suspended for 1 hour in 10 ml of anhydrous (distilled over 500 mg of cobalt trifluoride) hydrogen fluoride containing 1 ml of anisole.

The hydrogen fluoride was removed under reduced pressure and the anisole was removed by washing with diisopropyl ether (3×10 ml). The crude peptide was extracted from the resin with dimethylformamide (3×10 ml) and purified by gel filtration of Sephadex LH-20 using dimethylformamide as eluent, and by ion exchange chromatography on DEAE-Sephadex A-25 using as eluent ammonium acetate buffer at pH 6. The product was then transformed to the sodium salt with an excess of sodium bicarbonate, desalted on Sephadex G-15 and lyophilized.

0.130 g of peptide (2) were obtained.

E$_{5.8}$ 0.30.

Amino acid ratio: Asp 0.98; Ser 1.95; Glu 1.97; Pro 1.96; Gly 1.00; Leu 2.94; Ile 1.98.

EXAMPLE 3

H-Gly-Pro-Pro-Ile-Ser-Ile-Asp-Leu-Ser-Leu-Glu-Leu-OH sodium salt (165)

1 g of peptide resin obtained by procedure B with the required sequence of amino acid residues (introduced as Boc-Leu-OH, Boc-Glu(OBzl)-OH, Boc-Leu-OH, Boc-Ser(Bzl)-OH, Boc-Leu-OH, Boc-Asp(OBzl)-OH, Boc-Ile-OH, Boc-Ser(Bzl)-OH, Boc-Ile-OH, Boc-Pro-OH, Boc-Pro-OH, Boc-Gly-OH in that order) was suspended for 1 hour at 0° C. in 10 ml of anhydrous (distilled over 500 mg of cobalt trifluorid hydrogen fluoride containing 1 ml of anisole.

The hydrogen fluoride was removed under reduced pressure and the anisole was removed by washing with diisopropyl ether (3×10 ml). The crude peptide was extracted from the resin with dimethylformamide (3×10 ml) and purified by gel filtration on Sephadex LH-20 using dimethylformamide as eluent and by ion exchange chromatography on CH-Sephadex C-25 using as eluent ammonium acetate buffer at pH 4. The product was then transformed to the sodium salt with an excess of sodium bicarbonate, desalted on Sephadex C$_1$-15 and lyophilized.

0.110 g of peptide (165) were obtained.

Rf$_A$ 0.16, Rf$_B$ 0.44, E$_{5.8}$ 0.34; R$_t$ (HPLC)Ca. 17'

Amino acid ratio: Asp 0.98; Ser 1.97; Glu 1.00; Pro 1.99; Gly 0.99, Leu 2.97; Ile 1.98.

EXAMPLE 4

H-Gly-Pro-Pro-Ile-Ser-Ile-Asp-Leu-Ser-Leu-Glu-Leu-NH$_2$ sodium salt (166)

1 g of peptide resin obtained by procedure D with the required sequence of amino acid residues (introduced as Boc-Leu-OH, Boc-Glu (OBzl)-OH, Boc-Leu-OH, Boc-Ser(Bzl)-OH, Boc-Leu-OH, Boc-Asp(OBzl)-OH, Boc-Ile-OH, Boc-Ser(Bzl)-OH, Boc-Ile-OH, Boc-Pro-OH, Boc-Pro-OH, Boc-Gly-OH in that order) was suspended for 1 hour at 0° C. in 10 ml of anhydrous (distilled over 500 mg of cobalt trifluoride, hydrogen fluoride containing 1 ml of anisole.

The hydrogen fluoride was removed under reduced pressure and the anisole was removed by washing with diisopropyl ether (3×10 ml). The crude peptide was extracted from the resin with dimethylformamide (3×10 ml) and purified by gel filtration on Sephadex LH-20 using dimethylformamide as eluent and by ion exchange chromatography on CH-Sephadex C-25 using as eluent ammonium acetate buffer at pH4. The product was then transformed to the sodium salt with an excess of sodium bicarbonate, desalted on Sephadex G-15 and lyophilized.

0.110 g of peptide (166) were obtained.

E$_{5.8}$~0.

Amino acid ratio: Asp 0.98; Ser. 1.97; Glu 0.99; Pro 1.97; Gly 1.00; Leu 2.96; Ile 1.96.

EXAMPLE 5

Preparation of H-Gln-Glu-Pro-Pro-Ile-Ser-Leu-Asp-Leu-Thr-Phe-OH Sodium salt (89)

1 g of peptide-resin obtained by procedure B with the required sequence of amino acid residues (Boc-Phe-OH, Boc-Thr(Bzl)-OH, Boc-Leu-OH, Boc-Asp(OBzl)-OH, Boc-Leu-OH, Boc-Ser(Bzl)-OH, Boc-Ile-OH, Boc-Pro-OH-Boc-Pro-OH, Boc-Glu(OBzl)-OH, Boc-Gln-OH, in that order) was suspended for 1 hr at 0° C. in 10 ml of anhydrous (distilled over 500 mg of cobalt trifluoride) hydrogen fluoride containing 1 ml of anisole. The hydrogen fluoride was removed under reduced pressure and the anisole was removed by washing (3×10 ml) with diisopropyl ether. The crude peptide was extracted from the resin with dimethylformamide (3×10 ml) and purified by gel filtration of Sephadex LH-20 using dimethylformamide as eluent and by ion exchange chromatography on CH-Sephadex C-25 using as eluent ammonium acetate at pH4. The product was then converted to sodium salt with an excess of sodium bicarbonate, desalted on Sephadex G-15 and lyophilized.

0.130 g of peptide (89) were obtained.

Rf$_A$ 0.22, Rf$_B$ 0.45, E$_{5.8}$ 0.75 R$_t$ (HPLC)ca 12'

Amino acid ratio: Asp 0.99; Thr 0.88; Ser 0.96, Glu 1.98, Pro 1.98, Leu 2.00; Ile 0.98; Phe 0.99.

In similar way the following compounds were prepared:

(VI)

Pyr-Gly-Pro-Pro-Ile-Ser-Ile-Asp-Leu-Ser-Leu-Glu-OH sodium salt (45)

E$_{5.8}$ 0.63.

Amino acid ratio: Asp 0.98; Ser 1.96; Glu 1.98; Pro 1.99; Gly 1.00; Leu 1.97; ;L Ile 1.98.

(VII)

Pyr-Gly-Pro-Pro-Ile-Ser-Ile-Asp-Leu-Ser-Leu-Glu-NH$_2$ sodium salt (46)

E$_{5.8}$ 0.30.

Amino acid ratio: Asp 0.99; Ser 1.95; Glu 1.97; Pro 1.98; Gly 1.00; Leu 1.98; Ile 1.97.

(VIII)

Pyr-Gly-Pro-Pro-Ile-Ser-Ile-Asp-Leu-Ser-Leu-OH sodium salt (69)

E$_{5.8}$ 0.32.

Amino acid ratio: Asp 0.98; Ser 1.97; Glu 0.98, Pro 1.98, Gly 1.00, Leu 1.99.

(IX)

Pyr-Gly-Pro-Pro-Ile-Ser-Ile-Asp-Leu-Ser-Leu-NH$_2$ sodium salt (70)

E$_{5.8}$ 0.15.

Amino acid ratio: Asp 0.99, Ser 1.98; Glu 0.99; Pro 1.97; Gly 1.00; Leu 1.99; Ile 1.99.

(X) Pyr-Gly-Pro-Pro-Ile-Ser-Ile-Asp-Leu-Ser-OH sodium salt (91)

E$_{5.8}$ 0.35.

Amino acid ratio: Asp: 0,97; Ser 1.96; Glu 0.97; Pro 1.96; Gly 0.99; Leu 1.00; Ile 1.98.

(XI) Pyr-Gly-Pro-Pro-Ile-Ser-Ile-Asp-Leu-Ser-NH$_2$ sodium salt (92)

E$_{5.8}$ 0.16.

Amino acid ratio:

Asp 0.98, Ser 1.97; Glu 1.01; Pro 1.97; Gly 1.00; Leu 1.00; Ile 1.97.

(XII) H-Gly-Pro-Pro-Ile-Ser-Ile-Asp-Leu-Ser-OH sodium salt (111)

E$_{5.8}$ 0.18.

Amino acid ratio: Asp 0.99; Ser 1.98; Pro 1.99; Gly 1.01; Leu 1.00; Ile 1.99.

(XIII) H-Gly-Pro-Pro-Ile-Ser-Ile-Asp-Leu-Ser-NH$_2$ sodium salt (112)

$E_{5.8}$ ca. 0.
Amino acid ratio: Asp 0.98; Ser 1.98; Pro 1.98; Gly 0.99; Leu 1.00, Ile 1.98.

(XIV) H-Gly-Pro-Pro-Ile-Ser-Ile-Asp-Leu-Ser-Leu-OH sodium salt (127)

$E_{5.8}$ 0.15.
Amino acid ratio: Asp 0.99; Ser 1.97; Pro 1.99; Gly 1.00; Leu 1.99; Ile 1.98.

(XV) H-Gly-Pro-Pro-Ile-Ser-Ile-Asp-Leu-Ser-Leu-NH$_2$ sodium salt (128)

$E_{5.8}$ ca.0.
Amino acid ratio: Asp 0.98; Ser 1.97; Pro 1.97; Gly 1.00; Leu 2.00; Ile 1.99.

(XVI) H-Gly-Pro-Pro-Ile-Ser-Ile-Asp-Leu-Ser-Leu-Glu-OH sodium salt (145)

$E_{5.8}$ 0.32.
Amino acid ratio: Asp 0.99; Ser 1.98; Glu 0.97; Pro 1.98; Gly 1.00; Leu 2.01; Ile 1.99.

(XVII) H-Gly-Pro-Pro-Ile-Ser-Ile-Asp-Leu-Ser-Leu-Glu-NH$_2$ sodium salt (146)

$E_{5.8}$ 0.16.
Amino acid ratio: Asp 0.98; Ser 1.98; Glu 0.98; Pro 1.99; Gly 1.00; Leu 1.98; Ile 1.98.

(XVIII) Pyr-Gly-Pro-Pro-Ile-Ser-Ile-Asn-Leu-Ser-Leu-Glu-Leu-OH sodium salt (13)

$E_{5.8}$ 0.28.
Amino acid ratio: Asp 0.99; Ser 1.99; Glu 1.99; Pro 1.98; Gly 1.00; Leu 2.97; Ile 1.97.

(XIX) Pyr-Gly-Pro-Pro-Ile-Ser-Ile-Asn-Leu-Ser-Leu-Glu-Leu-NH$_2$ sodium salt (11)

$E_{5.8}$ 0.14.
Amino acid ratio: Asp 0.99; Ser 1.97; Glu 1.97; Pro 1.99; Gly 1.00; Leu 2.98; Ile 1.99.

(XX) Pyr-Gly-Pro-Pro-Ile-Ser-Ile-Asp-Leu-Ser-Leu-Gln-Leu-OH sodium salt (5)

$E_{5.8}$ 0.28.
Amino acid ratio: Asp 0.97; Ser 1.98; Glu 1.96; Pro 1.97; Gly 1.00; Leu 2.97; Ile 1.97.

(XXI) Pyr-Gly-Pro-Pro-Ile-Ser-Ile-Asp-Leu-Ser-Leu-Gln-Leu-NH$_2$ sodium salt (6)

$E_{5.8}$ 0.14.
Amino acid ratio:
Asp 0.98; Ser 1.97; Glu 1.97; Pro 1.99; Gly 1.00; Leu 3.01; Ile 1.99.

(XXII) Pyr-Gly-Pro-Pro-Ile-Ser-Ile-Asp-Leu-Ser-Leu-Glu-Phe-OH sodium salt (3)

$Rf_A$ 0.16; $Rf_B$ 0.42; $E_{5.8}$ 0.60.

Amino acid ratio: Asp 0.99; Ser 1.95; Glu 1.99; Pro 1.98; Gly 1.00; Leu 1.97; Ile 1.98; Phe 1.00.

(XXIII) Pyr-Gly-Pro-Pro-Ile-Ser-Ile-Asp-Leu-Ser-Leu-Glu-Phe-NH$_2$ sodium salt (4)

$E_{5.8}$ 0.30.
Amino acid ratio: Asp 0.98; Ser 1.98; Glu 1.96; Pro 1.98; Gly 1.01; Leu 1.99; Ile 1.98; Phe 1.00.

EXAMPLE 24 TO 186

Using corresponding starting materials and by way of corresponding intermediates, the peptides identified above by the numbers 7 to 12, 15 to 44, 47 to 68, 71 to 90, 93 to 110, 113 to 126, 129 to 144, 147 to 186 are obtained analogously to the aforegoing Examples.

What we claim is:

1. A peptide having a prolactin secretion inhibiting effect of the formula:

X-A-Pro-Pro-Ile-Ser-B-C-Leu-D-E-F-G-W, wherein X represents a hydrogen atom, Pyr, Gln, Pro or a 2-oxo-L-pipecolic acid residue,
A represents Glu, Gln or Gly,
B represents Ile, Leu, Nle, Val or Phe,
C represents Asn, Gln, Asp or Glu,
D represents Ser, Hse or Thr
E represents Phe, Leu or Nle, or a valence bond,
F represents Glu, Gln or His or a valence bond,
G represents Leu or Phe or a valence bond,
W represents a hydroxy group, or amino group or a group of the formula OR, NHR, NR$_2$ or NH—NH—R' wherein R represents methyl, ethyl, n-propyl, isopropyl, n-butyl, s-butyl, isobutyl, t-butyl, 2,2,2-trifluoroethyl, cyclohexyl, adamantyl, phenyl, benzyl and phenethyl groups,
R' represents hydrogen atom, allyl and pentenyl groups or any of the groups specifically named in this claim for R, or formyl, acetyl, trifluoroacetyl, propionyl, butyryl, adamantylcarbonyl, benzoyl, phenylacetyl and cinnamyl, or benzyloxycarbonyl (Z), 4-nitrobenzyloxycarbonyl, 4-methoxybenzyloxycarbonyl, 2,4-dichlorobenzyloxycarbonyl, 2-bromobenzyloxycarbonyl, 9-fluorenylmethoxycarbonyl (Fmoc) and 3,5-dimethoxy-α,α$^1$-dimethylbenzyloxycarbonyl (Ddz) groups; t-butyloxycarbonyl (Boc), 1-methyl-cyclobutyloxycarbonyl, adamantyloxycarbonyl and isobornyloxycarbonyl groups, or a pharmaceutically acceptable salt thereof.

2. A peptide according to claim 1 where W represents the OH group.

3. The peptide according to claim 1 where W represents the NH$_2$ group.

4. A protected peptide which is a peptide according to claim 1 protected at at least one of the (A) terminal nitrogen atom of group X, when X is an amino acid residue, or of group A, when A is a terminal amino acid residue, and the (B) alcoholic hydroxy group of the amino acid residue D.

5. A protected peptide according to claim 4 wherein the terminal nitrogen atom protecting group is formyl, acetyl, trifluoroacetyl, propionyl, benzoyl, benzyloxycarbonyl (Z), 4-nitrobenzyloxycarbonyl, 4-methoxybenzyloxycarbonyl, 2,4-dichlorobenzyloxycarbonyl, 2-bromobenzyloxycarbonyl, 9-fluorenylmethoxycarbonyl (Fmoc), 3,5-dimethoxy-α,α'-dimethylbenzyloxycarbonyl (Ddz), t-butyloxycarbonyl (Boc), 1-methyl-cyclobutyloxycarbonyl, adamantyloxycarbonyl, isobornyloxycarbon-1 groups, trityl, benzyl (B-1), methyl or isopropyl and the alcoholic hydroxy group protecting group is t-butyl, trityl, benzyl, 2,4-dichlorobenzyl, benzyloxycarbonyl, 2-bromobenzyloxycarbonyl, tetrahydropyranyl, t-butyloxycarbonyl, formyl, acetyl, trifluoroacetyl, propionyl or benzoyl.

6. A peptide which is H-Pyr-Gly-Pro-Pro-Ile-Ser-Ile-Asp-Leu-Ser-Leu-Glu-Leu-OH.

7. A pharmaceutical composition comprising an effective amount of a peptide or a pharmaceutically acceptable salt thereof as defined in claim 1 or 6 to inhibit prolactin secretion in admixture with a pharmaceutically acceptable diluent or carrier.

* * * * *